(12) United States Patent
Belder et al.

(10) Patent No.: US 6,596,238 B1
(45) Date of Patent: Jul. 22, 2003

(54) COATINGS WITH CROSS-LINKED HYDROPHILIC POLYMERS

(75) Inventors: Detlev Belder, Mülheim an der Ruhr (DE); Heribert Husmann, Mülheim an der Ruhr (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 09/634,770

(22) Filed: Aug. 9, 2000

(30) Foreign Application Priority Data

Aug. 11, 1999 (DE) .......................... 199 38 002

(51) Int. Cl.$^7$ ................................. B01L 3/02
(52) U.S. Cl. ..................... 422/100; 422/56; 204/479; 204/480; 204/451
(58) Field of Search ................. 204/451, 479, 204/480; 422/56, 100

(56) References Cited

U.S. PATENT DOCUMENTS 6,074,541 A * 6/2000 Srinivasan et al. ......... 204/451

* cited by examiner

*Primary Examiner*—Jill Warden
*Assistant Examiner*—Samuel P. Siefke
(74) *Attorney, Agent, or Firm*—Norris McLaughlin & Marcus

(57) ABSTRACT

The present invention relates to a process for permanently coating the inner surface of columns, capillaries and microchannel systems with hydroxylic polymers, such as polyvinyl alcohol, and to the thus prepared columns, capillaries and microchannel systems and their use.

2 Claims, 6 Drawing Sheets

Schematic representation of the experimental design for the coating of microchannels in CE-Chips

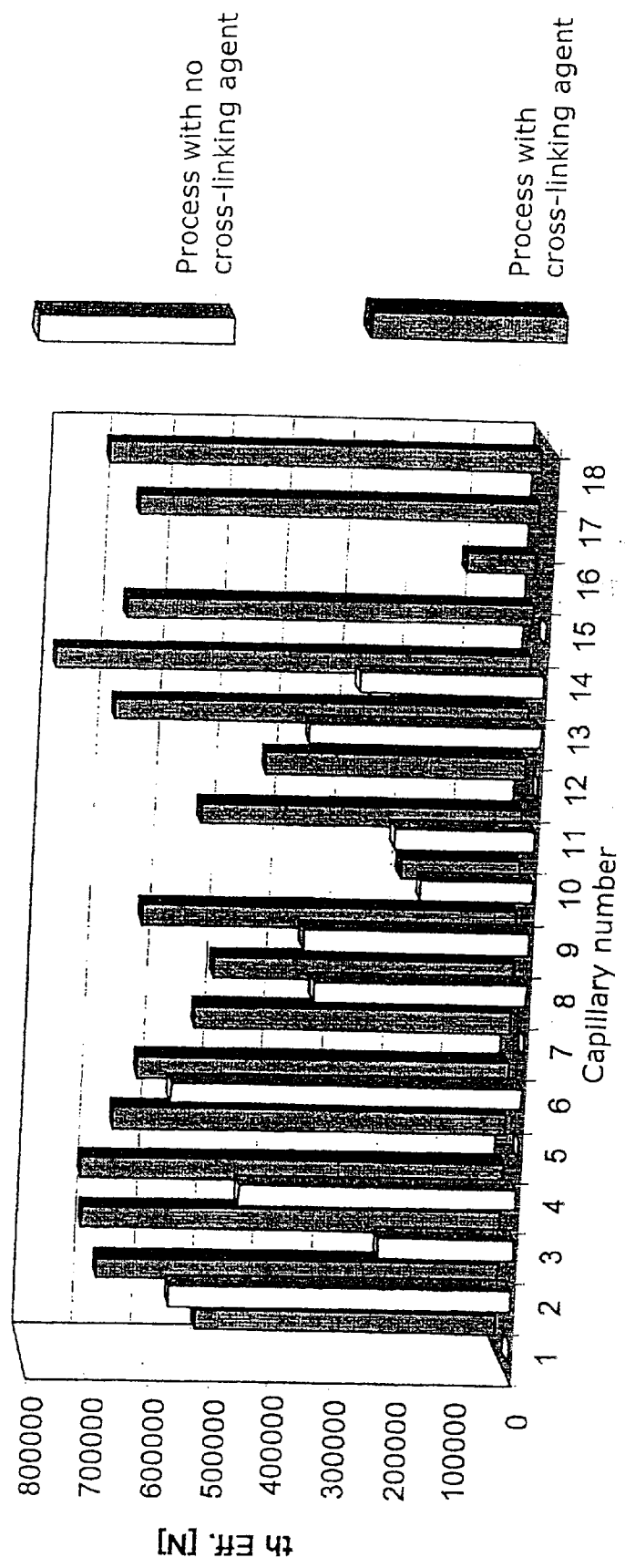
Figure 1: Comparison of the qualities of successive capillary coatings effected by the coating process using a cross-linking agent and an analogous process with no cross-linking agent. Efficiencies for cytochrome c obtained in CE separations

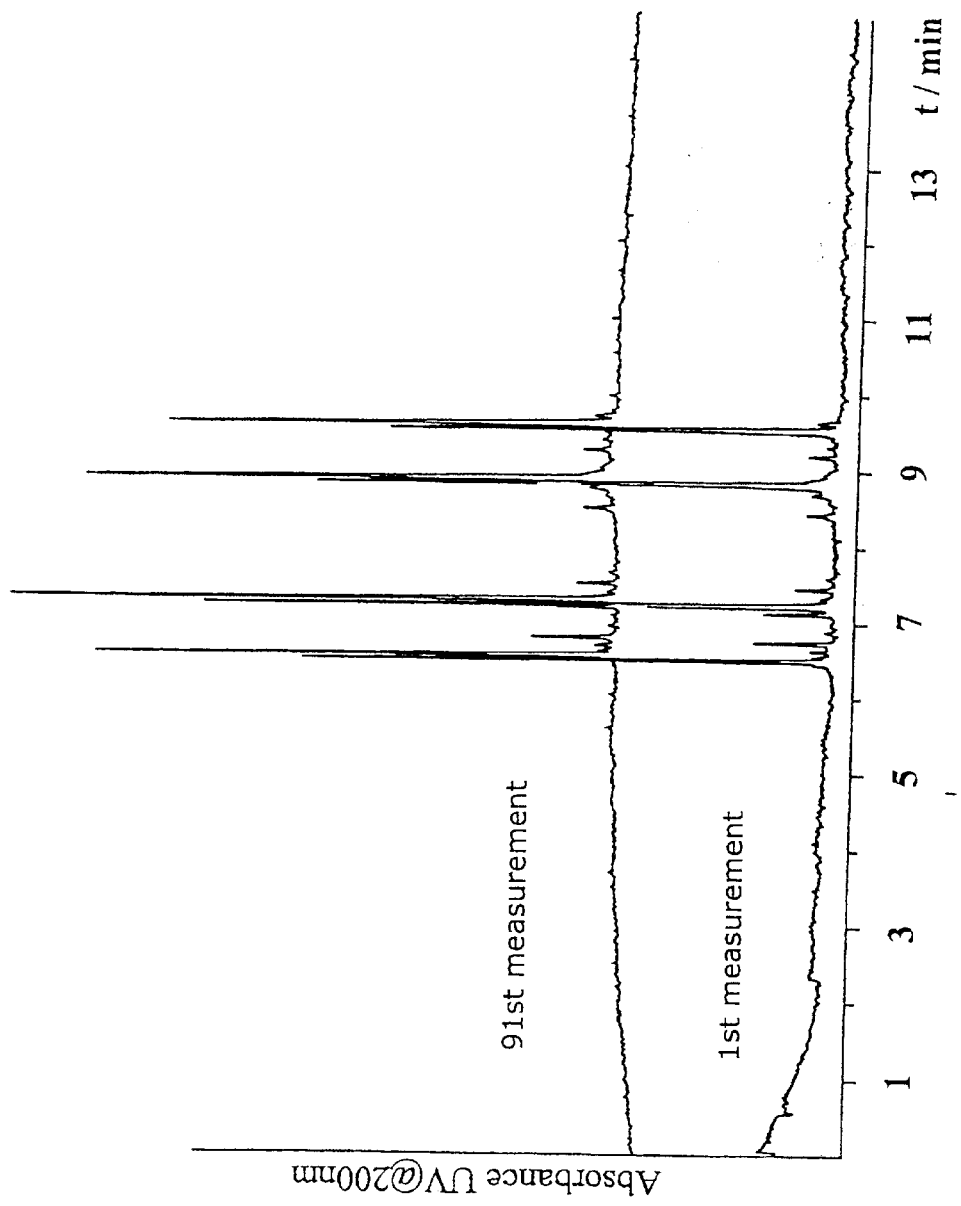
Figure 2: Reproducibility of CE separations of basic proteins in a PVA-coated capillary

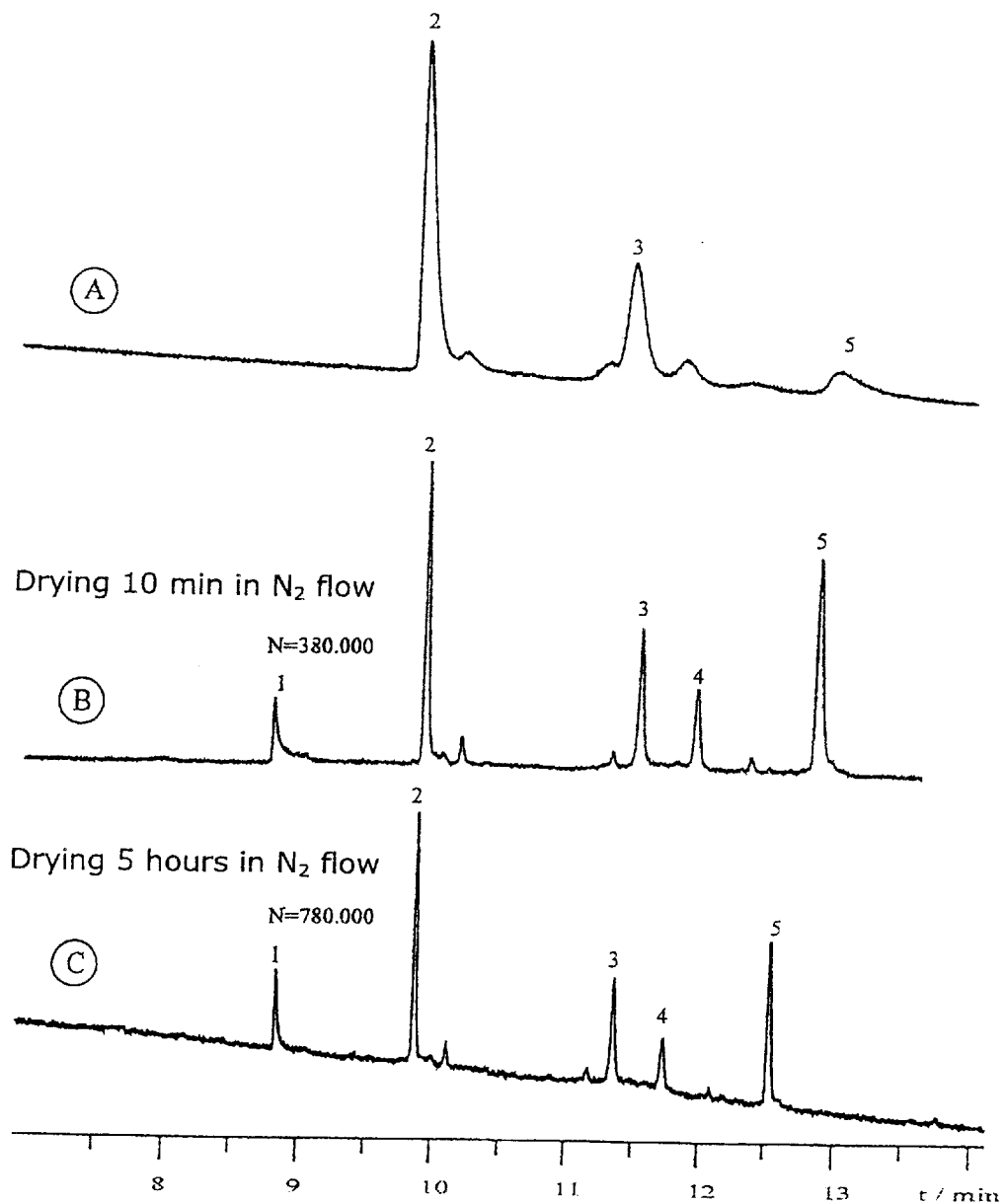
Figure 3: Comparison of CE separations of basic proteins with PVA-coated capillaries dried for different periods of time (B; C) and with an uncoated capillary (A)

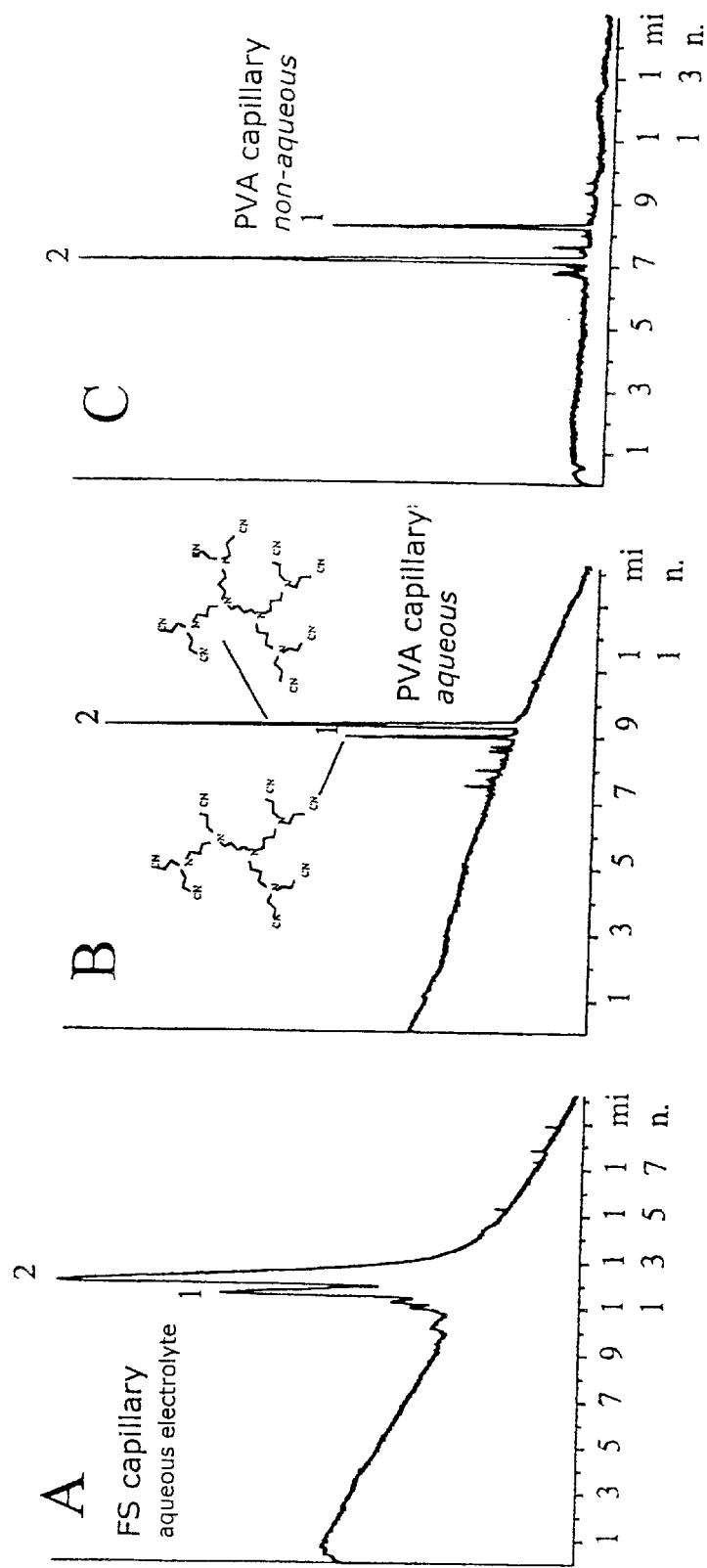
Figure 4: Use of a PVA capillary for the CE analysis of basic dendrimers in an aqueous (B) and a non-aqueous electrolyte (C) and comparison with a CE separation using an uncoated capillary (A)

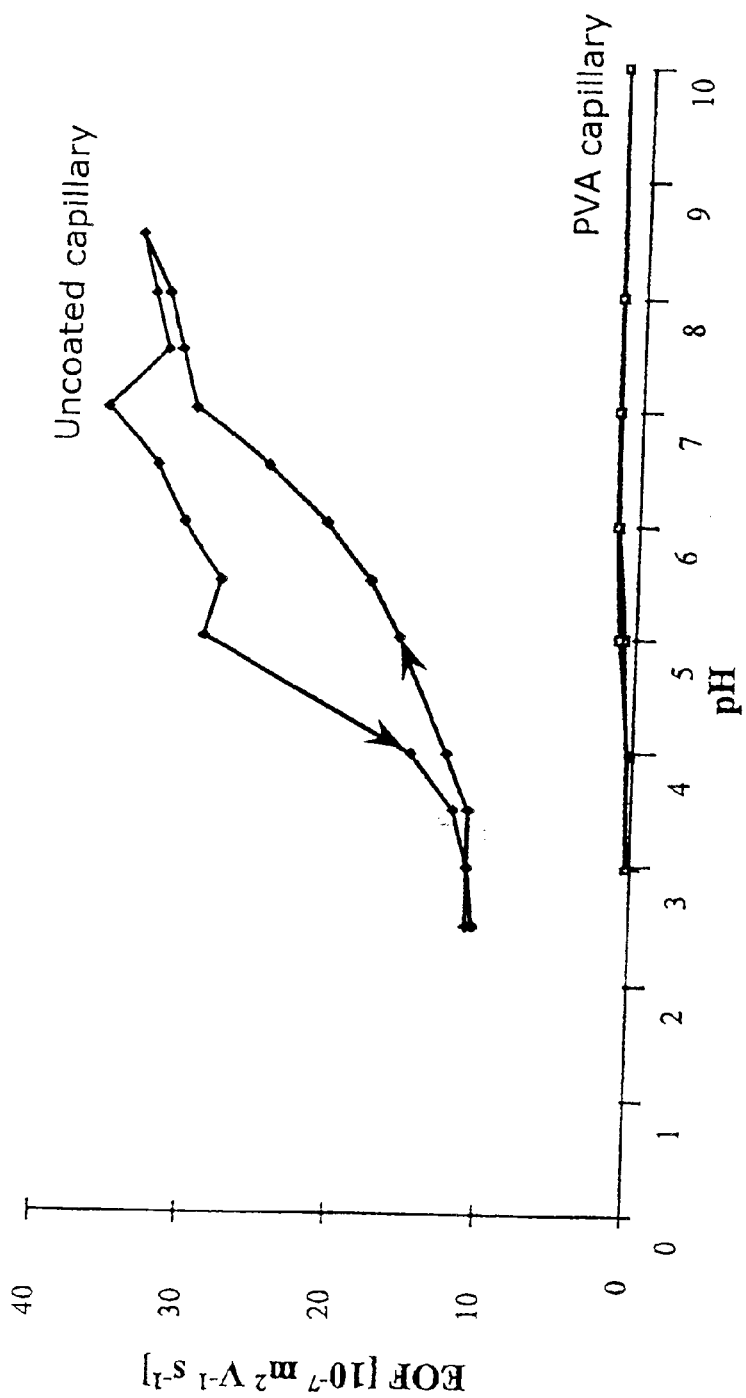
Figure 5: Influence of the electrolyte pH on the electroosmotic flow of a PVA capillary as compared with an uncoated capillary

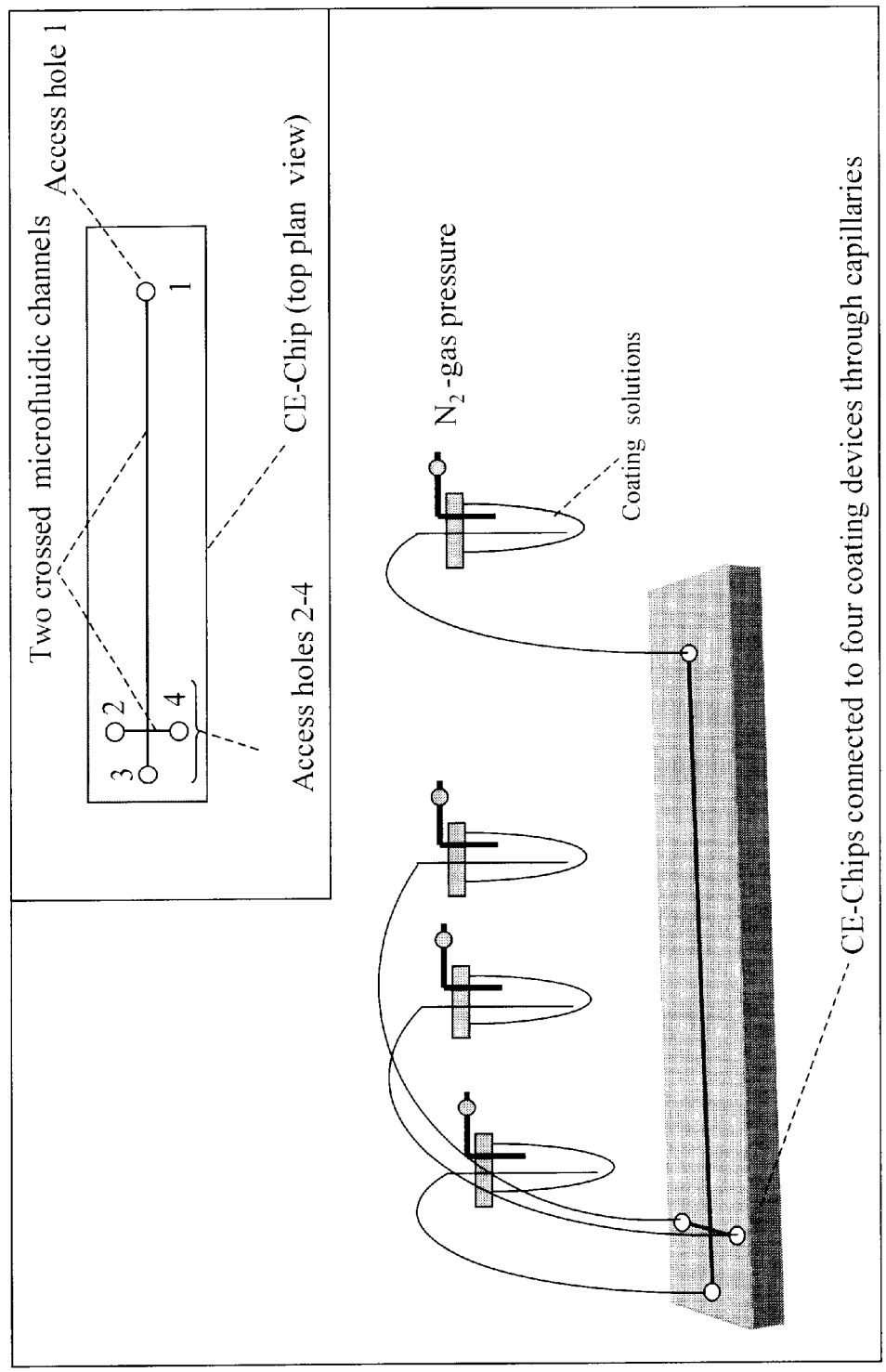
Fig. 6  Schematic representation of the experimental design for the coating of microchannels in CE-Chips

COATINGS WITH CROSS-LINKED HYDROPHILIC POLYMERS

The present invention relates to a process for permanently coating the inner surface of columns, capillaries and microchannel systems with hydroxylic polymers. Such interior coating is effected by treating the surface to be coated with a solution of a cross-linking reagent and a solution of the polymer, which results in an immobilization of the polymer on the capillary surface. The process described is particularly suitable for the coating of fused silica (FS) capillaries and systems having microfluidic structures for capillary electrophoresis with a highly hydrophilic polymer, such as polyvinyl alcohol. The invention further relates to the thus prepared columns and capillaries, and their use in capillary electrophoresis and related techniques.

BACKGROUND

Methods of capillary electrophoresis (CE) can be used to obtain separations of mixtures of various compounds by differential migration of the analytes in an electric field. The separations are usually performed in capillaries of fused silica filled with a, mostly aqueous, electrolyte. The inner surfaces of such capillaries have the following properties in their application in capillary electrophoresis:

Due to the acidic silanol groups of the fused silica material, there is an electroosmotic flow (EOF) towards the cathode which depends on the pH value of the electrolyte. However, in uncoated fused silica capillaries, the absolute value of the EOF can highly vary, which significantly deteriorates the precision and reproducibility of analyses in capillary electrophoresis.

The fused silica surfaces exhibit a highly adsorptive behavior towards many compounds. In particular, basic compounds and large biopolymers, such as proteins, are strongly adsorbed from aqueous solutions. This deteriorates the quality and resolution of a capillary-electrophoretic separation of such compounds considerably or even makes it impossible.

The properties of such capillaries can be changed in a well-aimed manner by providing the capillary surface with a suitable coating. Coated fused silica capillaries are employed in capillary electrophoresis for the following reasons:

For a manipulation of the electroosmotic flow: By coating the surface, both the absolute value and the direction of the EOF can be changed. A CE separation can be optimized thereby with respect to resolution and analysis time. The constancy of the EOF is mostly higher in coated capillaries as compared to untreated fused silica capillaries, which results in improved reproducibility of CE analyses.

To suppress the interactions between analytes and the wall, coatings are employed which exhibit a low adsorptivity towards the compounds to be examined. Higher separation efficiencies of adsorptive compounds, such as proteins, and thus a better resolution is thereby achieved in capillary-electrophoretic separations.

A suitable inner coating of capillaries for CE should have the following properties: i) a constant EOF over a broad pH range; ii) long-term stability towards a wide variety of electrolytes; iii) the adsorptivity of the coating should be as low as possible towards a wide variety of analytes.

Fused silica capillaries can be very easily coated with cationic polymers, such as Polybrene® or polyvinylamine [M. Chiari, L. Ceriotti, G. Crini, and M. Morcellet; J. Chromatogr. A 836(1999) 81], because these are strongly adsorbed to the contrarily charged fused silica surfaces. Due to the reversed, anodic EOF, these capillaries are particularly suitable for the accelerated analysis of highly mobile anions.

The use of hydrophilic non-ionic capillary interior coatings, such as polyacrylamide or polyethylene glycol coatings, has proven particularly useful in capillary electrophoresis, because such coatings both significantly reduce the EOF and suppress the adsorption of basic compounds and especially proteins to the capillary wall. Different methods have been developed for chemically binding hydrophilic molecules to a fused silica capillary surface, mostly after previous silanization (S. Hjerten; J. Chromatogr. 347 (1985) 191; G. M. Bruin, J. P. Chang, R. H. Kuhlmann, K. Zegers, J. C. Kraak and H. Poppe; J. Chromatogr. 471 (1989) 429; K. A. Cobb, V. Dolnik and M. Novotny; Anal. Chem. 62 (1990) 2478; A. Malik, Z. Zhao and M. L. Lee; J. Microcol. September 5 (1993) 119).

Among all the capillary coatings described in the literature, those based on polyvinyl alcohol (PVA), which has to be considered the most hydrophilic polymer, have proven to exhibit a particularly good performance. In capillaries coated with PVA, extraordinarily high separation efficiencies could be achieved, especially for proteins. In addition, the electroosmotic flow is suppressed over a broad pH range and very stable (M. Gilges, H. Kleemiβ and G. Schomburg; Anal. Chem. 66 (1994) 2038).

PRIOR ART

The preparation of capillaries coated with polyvinyl alcohol is relatively difficult to perform with conventional methods. This is due to the particular properties of polyvinyl alcohol: i) Polyvinyl alcohol is soluble only in water, and therefore classical chemical reactions in organic solvents for fixing the polymer to the capillary surface, such as by silanization, are not possible. ii) Due to their high hydrophilicity, aqueous solutions of polyvinyl alcohol will wet the fused silica capillaries but poorly; therefore, it is difficult to produce homogeneous films of polyvinyl alcohol on the capillary surfaces by adsorption alone. To date, the following methods have been described for producing PVA-coated capillaries:

1) Gilges and Schomburg (M. Gilges, H. Kleemiβ and G. Schomburg; Anal. Chem. 66 (1994) 2038; DE 42 30 403 A1) have applied a PVA film to a capillary wall by adsorption of polyvinyl alcohol from an aqueous solution to the fused silica surface. Thus, a capillary filled with the PVA solution was emptied very slowly in a nitrogen flow using overpressure. Only by carefully and very slowly emptying the capillary, a homogeneous polymer film could be produced on the surface despite the poor wetting of the surface by the polymer solution. In the original publication (Anal. Chem. 66 (1994) 2038), a flow-restricting capillary was coupled to the capillary to be coated for a controlled emptying.

The immobilization of the polymer film, which is water-soluble at first, was then effected by heating in a gas flow. Polyvinyl alcohol is thereby converted to a pseudocrystalline state and thus insoluble in water.

With this method, stable polyvinyl alcohol coatings could be applied to the capillaries without expensive multistep chemical reactions. However, since the polymer film is applied in this method from a polymer solution which wets the fused silica wall but very poorly, this part of the process is rather error-prone.

2) Shieh (U.S. Pat. No. 5,605,613) was able to prepare PVA-coated capillaries in a multistep process. Thus, a hydrophobic intermediate layer was first bound to the fused silica surface through Si—O—Si linkages. Polybutadienyltriethoxysilane was mentioned as a preferred reagent. Thereafter, the monomer vinyl acetate is bound to this layer through its vinyl functionality by free-radical polymerization. Subsequently, the polyvinyl acetate covalently bonded to the intermediate layer is hydrolyzed and thus converted to polyvinyl alcohol.

The procedure described by Shieh is based on a lengthy multistep reaction. The first step is based on a silanol derivatization and is therefore highly dependent on the concentration of silanol groups on the fused silica surface and thus on the respective capillary preparation process and/or the chosen preliminary treatment of the capillary.

3) The method described by Karger (U.S. Pat. No. 5,840,388) is very similar to that described by Shieh. An intermediate layer which will react with the monomer vinyl acetate is also first applied through Si—O—Si linkages by a silanization reaction in organic solvents, preferably using vinyltrimethoxysilane. Then, as in Shieh, covalently bonded polyvinyl acetate is generated in a free-radical copolymerization reaction of the intermediate layer with vinyl acetate. Then, following hydrolysis, polyvinyl alcohol covalently bonded to the silica surface is obtained by analogy with Shieh.

SUMMARY OF THE INVENTION

It has been the object of the invention to provide a quick and reliable process for coating capillaries with hydroxylic polymers, preferably polyvinyl alcohol, and their use in electromigrative separation methods.

This object of permanently coating a capillary with a polymer, preferably polyvinyl alcohol, is achieved by chemically cross-linking the dissolved polymer during the coating process and thus immobilizing it on the capillary wall. Thus, a dissolved bi- or multifunctional reagent, preferably a dialdehyde, such as glutaraldehyde, is transferred into the capillary. Thereafter, a plug of the polymer solution, preferably a polyhydroxy compound, such as polyvinyl alcohol, is forced through the capillary, for example, using a pressurized gas, such as nitrogen or other gases usual in a laboratory, e.g., helium, argon, hydrogen, or by means of a mercury plug. The reaction occurring between the polymer solution and the cross-linking reagent enables a good wetting of the capillary wall with the polymer solution and at the same time immobilizes the produced polymer layer on the capillary wall. The thus generated very stable polymer coatings can be employed immediately after drying by additional flushing with gas, and exhibit the following properties in capillary electrophoresis: suppressed EOF both in acidic and alkaline pH ranges, very high separation efficiencies for adsorptive analytes, such as basic proteins, long-term stability upon use of aqueous and non-aqueous electrolytes, stability towards highly acidic and alkaline rinsing solutions, such as diluted HCl or NaOH solutions.

This process enables PVA-coated capillaries of high quality to be prepared very quickly and with a high reliability. The coating process takes a few minutes, and the drying of the capillaries is effected in a nitrogen flow over several hours. The drying time can be significantly reduced by increasing the temperature so that the capillaries can be available in less than an hour.

Capillaries coated with PVA and glutaraldehyde as a cross-linking reagent in accordance with the present process can be prepared with substantially higher reliability as compared to the analogous process with no cross-linking reagent (with exclusively thermal immobilization). FIG. 1 shows the separation efficiencies achievable in CE separations of basic proteins for different capillaries prepared successively. If glutaraldehyde is used as the cross-linking reagent, very high separation efficiencies (N>400,000) for the strongly basic protein cytochrome c can be achieved in over 80% of the capillaries prepared.

However, if the coating is effected without the cross-linking reagent, separation efficiencies N of greater than 400,000 are obtained in only 20% of the capillaries prepared. In 30% of the capillaries thus prepared (Nos. 1, 5, 12, 15), no signal can be obtained for the strongly adsorptive protein, because it was irreversibly adsorbed as with uncoated capillaries.

In addition to classical capillaries, surfaces of systems having microfluidic structures, such as microchannels of a capillary electrophoresis chip (CE chip), can also be coated with the present process. Thus, it becomes possible to suppress the electroosmotic flow in CE chips and to prevent the adsorption of analytes such as proteins. By selectively coating individual microchannels of a more complex system while others remain uncoated, electroosmotically induced liquid flows in networks of microchannels can be manipulated in a well-aimed way. Thus, for CE chips with crossed microchannels, it is possible to coat only the main channel relevant to the separation and thus to enable the analysis of adsorptive proteins while the injection channel remains uncoated and enables electroosmotic injection in the direction towards the cathode.

The present process for the preparation of polymer-coated capillaries is characterized by the following properties:

Since the process is based on chemical cross-linking of the polymer and chemical binding of the polymer to the capillary wall is not required, it can be applied to a wide variety of capillary materials, such as glass, fused silica, various plastics, such as Teflon, pEEK, polyacrylates, and it is also applicable to channels having different structures, such as classical round capillaries, (rect)angular channels/capillaries and microchannels in microfluidic systems (such as CE chips).

The process is easy to perform.

The process is very quick.

The capillaries obtained can be repeatedly prepared in a very high quality (few rejections).

The coated capillaries prepared by this process have the following properties:

They can be repeatedly employed for separations.

They allow for CE separations of highly adsortive compounds such as proteins in acidic, neutral and alkaline electrolytes.

The electroosmotic flow is highly reduced over a broad pH range, at least from pH 2 to pH 10, and is highly constant.

The chemically immobilized PVA coatings have proven stable under the conditions of CE.

The capillaries are especially suitable for the following applications: CE separations of basic and acidic compounds, capillary gel electrophoresis, isoelectric focusing, CE separations with very low ionic strengths of the electrolyte, and CE separations with organic solvents as electrolytes, such as for the coupling of capillary electrophoresis with mass spectrometry.

The capillaries and microfluidic systems prepared according to the invention can be employed, inter alia, for the dosage of samples to be analyzed, e.g., in mass spectrometry, and for microsynthetic methods in chemistry.

EXAMPLE 1
Coating of a Capillary with PVA with Thermal Aftertreatment

To prepare a separation column suitable for capillary electrophoresis, a commercially available fused silica capillary of 50 μm inner diameter and 75 cm length (manufacturer: Poly-Micro, Phoenix, Ariz., USA) was connected with a coating apparatus for subsequent coating. Then, a glutaraldehyde solution (200 μl of a 50% aqueous solution, mixed with 300 μl of 1:10 diluted conc. HCl) was pressed into the column with 0.5 MPa of nitrogen for 5 seconds. Immediately afterwards, a PVA solution (450 μl of a 5% aqueous PVA solution, mixed with 50 μl of 1:1 $H_2O$-diluted HCl) (PVA: MW about 90,000, 99+% hydrolyzed, Aldrich) was pressed into the column with 0.5 MPa for 10 seconds. Both liquid plugs were subsequently transported further through the column with 0.5 MPa. After 1–2 minutes, they had left the column, and the coating obtained was predried in a nitrogen flow for 10 minutes. Thereafter, the capillary was incorporated in a heatable oven (gas chromatography for accelerated drying and connected with the injector. While the column was flushed in a nitrogen flow (0.15–0.20 MPa), the oven was heated from 40° C. to 160° C. with 6° C./min. After cooling and removal of the column, it was ready for use. Prior to using it in a CE device, a UV-transmissive window was generated in the capillary at the appropriate position by scraping off the outer polyimide layer, and the capillary was brought to the desired length by truncating it at the front and back ends by about 10 cm each.

In a capillary prepared by the above described process and having the effective length 40.5 cm, the total length 54 cm and an inner diameter of 50 μm, a mixture of the following proteins was analyzed repeatedly: cytochrome c, lysozyme, trypsinogen and α-chymotrypsinogen. The separation was effected in an aqueous phosphate buffer at a concentration of 40 mM at pH 3 and a voltage of 20 kV. In FIG. 2, the first and the 91st of the separations obtained have been plotted over one another. It can be seen that very good, reproducible separations are obtained with these capillaries.

EXAMPLE 2
PVA Capillaries with No Thermal Aftertreatment

Two capillaries were coated with PVA by analogy with Example 1, but without the subsequent thermal treatment. Two freshly coated capillaries were dried in a nitrogen flow for different periods of time, and the capillaries obtained were then tested for use in capillary electrophoresis by analogy with Example 1. The test mixture consisted of basic proteins: (1) cytochrome c, (2) lysozyme, (3) trypsin, (4) trypsinogen, and (5) α-chymotrypsinogen. The electropherograms obtained and a comparison with a separation obtained in an uncoated capillary are shown in FIG. 3. In an uncoated capillary, efficient separations cannot be obtained due to strong adsorption of the proteins; the highly adsorptive protein cytochrome c is even completely adsorbed and does not elute from the column, see FIG. 3A. With a PVA capillary prepared according to the present process, highly efficient signals from all test compounds are obtained. If the drying of the PVA coating is performed for 5 hours in a gas flow, very efficient and stable columns are obtained after the coating has dried. If drying in a gas flow is performed for only 10 minutes, the separation efficiencies N (in numbers of theoretical plates) are lower for strongly adsorptive compounds such as cytochrome c.

EXAMPLE 3
Capillary-electrophoretic Separation of Basic Dendrimers

With a capillary prepared by analogy with Example 1, basic dendrimers were analyzed. These compounds are highly adsorptive with respect to fused silica. Therefore, an uncoated capillary can provide only a poor CE separation due to the peak broadening of the adsorbed analytes, see FIG. 4A. However, if the separation is effected with the same experimental parameters, but with a PVA-coated capillary, adsorption of the compounds to the capillary wall is effectively suppressed, and very sharp signals are obtained. This is shown in FIG. 4B.

PVA capillaries can also be run with electrolytes containing very high proportions of organic solvents, which is necessary, in particular, for the coupling of CE with a mass spectrometer (MS). The CE separation of dendrimers in an MS-compatible electrolyte is shown in FIG. 4C.

Experimental Conditions

Analyte concentration: 1 mg/ml, voltage: 15 kV, detection: UV 200 nm, electrolytes: A, B: 40 mM Na phosphate, C: 45% methanol, 10% water, 45% acetonitrile, 20 mM ammonium acetate.

EXAMPLE 4
Suppression of EOF Over a Broad pH Range

With a capillary prepared by analogy with Example 1, the dependence of the electroosmotic flow on the pH value of an aqueous electrolyte was determined. Thus, Na phosphate buffers were titrated to the corresponding pH values; the electroosmotic flow was determined from the migration time of the neutral marker DMSO. In FIG. 5, the results obtained for a PVA capillary are compared with the corresponding results for an uncoated capillary. In a capillary coated with PVA by the present process, the EOF is suppressed over a broad pH range, and in contrast to uncoated capillaries, it is almost independent of the pH value.

EXAMPLE 5
Coating of the Microchannels of a CE Chip

A CE chip of borofloat glass with microfluidic channels (20 μm depth, 50 μm width, length of injection channel: 8 mm; length of main channel: 85 mm) supplied by Micralyne (Edmonton, Canada) was coated with PVA according to the present process. Thus, the chip was placed in a fixture with seals, and each of the 4 openings was respectively connected in a gas-tight way through capillaries with a coating apparatus. This is schematically shown in FIG. 6. Using the coating apparatus, liquids or gases can be moved by pressure through the microfluidic structures of the chip.

To coat all channels in the chip, the channels in the chip were first completely filled with water. Then, a glutaraldehyde solution (200 μl of a 50% aqueous solution, mixed with 300 μl of 1:10 diluted conc. HCl) was pressed through a fused silica capillary (inner diameter 50 μm, length 30 cm) into opening 1 of the microchip with 0.5 MPa of nitrogen, while the capillaries on openings 2, 3 and 4 were without pressure (see FIG. 6). Immediately thereafter, a PVA solution (450 μl of a 3% aqueous PVA solution, mixed with 50 μl of 1:1 $H_2O$-diluted HCl) (PVA: MW about 90,000, 99+% hydrolyzed, Aldrich) was pressed through the capillary into opening 1 of the chip with 0.5 MPa for 10 seconds. Both liquid plugs were subsequently transported further through the channels of the chip with 0.5 MPa. After 1–2 minutes, they had left the microfluidic channels of the chip through openings 2, 3 and 4. Thereafter, 0.5 MPa of nitrogen was applied to openings 2, 3 and 4, while the pressure was released from opening 1 in order to flush the channels with gas. The layer formed on the surfaces of the channels was thus predried in a nitrogen flow for 15 minutes. Thereafter, the chip was incorporated in a heatable oven (gas chromatograph) together with the fixture and the capillaries for accelerated drying, and the capillary at opening 1 was connected with the injector. While the channels were flushed in a nitrogen flow (0.15–0.20 MPa), the oven was heated from 40° C. to 80° C. with 6° C./min. After cooling and removal of the chip, it was ready for use. CE chips with thus coated microchannels are characterized by a suppressed electroosmotic flow in both of the crossed channels.

EXAMPLE 6
Coating of Selected Microchannels of a CE Chip

According to the present process in combination with the experimental design described in Example 5, individual selected channels of systems with microfluidic structures can also be coated. Thus, in a CE chip with two crossed channels, it is possible to coat only one channel with PVA while the other remains uncoated and therefore, a strong EOF is present only in that latter channel.

For exclusively coating the main channel (channel between openings 1 and 3, see FIG. 6) in which the electrophoretic separation takes place while the shorter channel for sample injection (channel between openings 2 and 4, see FIG. 6) remains uncoated, the chip was connected with 4 coating apparatus by analogy with Example 5, and the channels were completely filled with water. Then, a glutaraldehyde solution (200 µl of a 50% aqueous solution, mixed with 300 µl of 1:10 diluted conc. HCl) was pressed through a fused silica capillary (inner diameter 50 µm, length 30 cm) into opening 1 of the microchip with 0.5 MPa of nitrogen, while water was introduced with a pressure of 0.1 MPa through the capillaries at openings 2 and 4 (see FIG. 6). After the glutaraldehyde solution left the capillary at opening 3, a PVA solution similar to that used in Example 5 was pressed through the capillary into opening 1 of the chip with 0.5 MPa for 10 seconds, while flushing with water was again effected through openings 2 and 4. The PVA liquid plug was subsequently transported further through the main channel of the chip in a nitrogen flow with 0.5 MPa. After 1–2 minutes, it had left the main channel of the chip through the capillary at opening 3. Thereafter, 0.5 MPa of nitrogen was applied to openings 2, 3 and 4, while the pressure was released from opening 1 in order to flush the channels with gas. The layer formed on the surfaces was subsequently dried as in Example 5.

CE chips with a thus coated main channel are characterized by a suppressed electroosmotic flow in that channel, while a strong cathodic flow was present in the sample injection channel.

What is claimed is:

1. A capillary having immobilized on an inner surface thereof a layer comprising a hydrophilic polymer cross-linked with an aldehyde or ketone produced by the process comprising immobilizing a dissolved hydroxylic polymer on the capillary or tube inner surface by chemical cross-linking of the polymer with a cross-linking reagent without covalent bonding of the polymer to the capillary or tube inner surface.

2. The capillary according to claim 1, wherein said hydrophilic polymer is polyvinyl alcohol.

* * * * *